United States Patent
Yamaki et al.

(10) Patent No.: US 10,426,714 B2
(45) Date of Patent: Oct. 1, 2019

(54) SPRAYABLE SUNSCREEN COSMETIC

(71) Applicant: SHISEIDO COMPANY, LTD., Tokyo (JP)

(72) Inventors: Satoshi Yamaki, Yokohama (JP); Taichi Harada, Yokohama (JP); Takashi Matsuda, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 15/765,012

(22) PCT Filed: Oct. 7, 2016

(86) PCT No.: PCT/JP2016/079962
§ 371 (c)(1),
(2) Date: Mar. 30, 2018

(87) PCT Pub. No.: WO2017/061604
PCT Pub. Date: Apr. 13, 2017

(65) Prior Publication Data
US 2019/0046421 A1    Feb. 14, 2019

(30) Foreign Application Priority Data

Oct. 9, 2015 (JP) ................................ 2015-201595
Oct. 6, 2016 (JP) ................................ 2016-198402

(51) Int. Cl.

| | | |
|---|---|---|
| A61K 8/06 | (2006.01) | |
| A61K 8/37 | (2006.01) | |
| A61K 8/40 | (2006.01) | |
| A61K 8/41 | (2006.01) | |
| A61K 8/49 | (2006.01) | |
| A61K 8/73 | (2006.01) | |
| A61K 8/891 | (2006.01) | |
| A61K 8/894 | (2006.01) | |
| A61Q 17/04 | (2006.01) | |
| A61K 8/26 | (2006.01) | |
| A61K 8/58 | (2006.01) | |
| A61K 8/60 | (2006.01) | |
| A61K 8/02 | (2006.01) | |
| A61K 8/04 | (2006.01) | |
| A61K 8/86 | (2006.01) | |

(52) U.S. Cl.
CPC ............ *A61K 8/064* (2013.01); *A61K 8/025* (2013.01); *A61K 8/0254* (2013.01); *A61K 8/046* (2013.01); *A61K 8/26* (2013.01); *A61K 8/37* (2013.01); *A61K 8/4966* (2013.01); *A61K 8/585* (2013.01); *A61K 8/60* (2013.01); *A61K 8/86* (2013.01); *A61K 8/891* (2013.01); *A61K 8/894* (2013.01); *A61Q 17/04* (2013.01); *A61K 2800/48* (2013.01); *A61K 2800/592* (2013.01); *A61K 2800/612* (2013.01)

(58) Field of Classification Search
None
See application file for complete search history.

(56) References Cited

U.S. PATENT DOCUMENTS

| | | | |
|---|---|---|---|
| 2005/0142079 A1* | 6/2005 | Garrison | ............... A61K 8/35 424/59 |
| 2007/0269389 A1* | 11/2007 | Fuscelli Pytel | ...... A61K 8/0229 424/59 |
| 2012/0156149 A1 | 6/2012 | Yamaguchi et al. | |
| 2012/0196942 A1 | 8/2012 | Yamaguchi et al. | |
| 2012/0201905 A1 | 8/2012 | Mune et al. | |
| 2012/0269875 A1 | 10/2012 | Tamura et al. | |
| 2012/0288458 A1 | 11/2012 | Yamaguchi et al. | |
| 2013/0121939 A1 | 5/2013 | Fukuhara | |
| 2014/0010775 A1 | 1/2014 | Sonoyama et al. | |
| 2014/0205552 A1 | 7/2014 | Fukuhara | |
| 2016/0058677 A1* | 3/2016 | Kitajima | ................. A61K 8/25 514/770 |

FOREIGN PATENT DOCUMENTS

| | | |
|---|---|---|
| EP | 2 915 524 | 9/2015 |
| JP | A-HEI 1180237 | 7/1989 |

(Continued)

OTHER PUBLICATIONS

Notice of Reasons for Revocation dated Nov. 14, 2018, 28 pages—English.
Fragrance Journal 1999-5, Rayleigh, Proc. Roy Soc. 84A; Kingerty W.O. Bowen, H.K. and Uhlman, 1 page—English, 5 pages—Japanese (pp. 79-83).

(Continued)

*Primary Examiner* — Brian Gulledge
(74) *Attorney, Agent, or Firm* — Andrew F. Young, Esq.; Lackenbach Siegel, LLP

(57) ABSTRACT

A sprayable sunscreen cosmetic contains substantially no ultraviolet ray scattering agents which cause whiteness, and which is transparent immediately after being applied/sprayed, and that has excellent ultraviolet ray protection effect and a good sensation in use. The ultraviolet ray protection effect is not reduced, and the effects improve when in contact with water. A water-in-oil emulsified sunscreen cosmetic comprises: (A) 6 to 40 mass % of an ultraviolet ray absorbing agent; (B) an organically modified clay mineral; (C) an oil phase thickener other than the aforementioned (B); (D) a silicone-based surfactant having an HLB of less than 8; (E) a spherical resin powder; and (F) a volatile silicone oil; wherein a ratio defined as [total amount of ingredient (B) and ingredient (C)]/[total amount of (G) non-volatile liquid oils other than silicone oils] is at least 0.04 and less than 0.68.

8 Claims, No Drawings

(56) References Cited

FOREIGN PATENT DOCUMENTS

| JP | A HEI 8217619 | 8/1996 |
| JP | H8-217619 | 8/1996 |
| JP | H08217618 | 8/1996 |
| JP | H9239259 | 9/1997 |
| JP | H09255543 | 9/1997 |
| JP | 9-301823 | 11/1997 |
| JP | 10-513188 | 12/1998 |
| JP | 2000-63233 | 2/2000 |
| JP | 2000063233 | 2/2000 |
| JP | 2000-72646 | 3/2000 |
| JP | 2001187711 | 7/2001 |
| JP | 2002-193741 | 7/2002 |
| JP | 2004-83541 | 3/2004 |
| JP | 2004091374 | 3/2004 |
| JP | 2005053846 | 3/2005 |
| JP | 2007-217380 | 8/2007 |
| JP | 2007-332295 | 12/2007 |
| JP | 2007332295 | 12/2007 |
| JP | 2009-40738 | 2/2009 |
| JP | WO2011049248 | 3/2011 |
| JP | 2011-126832 | 6/2011 |
| JP | 2011111401 | 6/2011 |
| JP | 2011126832 | 6/2011 |
| JP | 2011-153079 | 8/2011 |
| JP | 2012-188-394 | 10/2012 |
| JP | 2012-197241 | 10/2012 |
| JP | 2012197241 | 10/2012 |
| JP | 2012-219029 | 11/2012 |
| JP | 2014084318 | 5/2014 |
| JP | 2014088369 | 5/2014 |
| JP | 2014201541 | 10/2014 |
| JP | 2014224075 | 12/2014 |
| JP | 2017-71602 | 4/2017 |
| JP | 6263244 | 12/2017 |
| WO | WO2009/119000 | 10/2009 |
| WO | WO 2011/049248 | 4/2011 |
| WO | WO-2014136886 A1 * | 9/2014 ............... A61K 8/25 |

OTHER PUBLICATIONS

Tamura Takeo "Cosmetics Science" (issued 3$^{rd}$ Edition, Jun. 10, 1978), Japan Society of Hair Sciences 122-125 (Annex 9), 4 pages—Japanese; 2 pages—English.

JP2016-198402, Appeal Brief, dated Oct. 17, 2017, 9 pages—English, 7 pages—Japanese.

JP-B-6263244, Certificate of Translation of Granted Claims dated May 9, 2018, 1 page—English.

JP2016-198402, Decision of Rejection, dated Jun. 9, 2017, 7 pages—English, 7 pages—Japanese.

JP2016-198402, Decision to Grant Patent, dated Dec. 1, 2017, 3 pages—English, 3 pages—Japanese.

JP2016-198402, Demand for Appeal, dated Sep. 8, 2017, 3 pages—English, 4 pages—Japanese.

JP-B-6263244, Granted Claims, 2 pages—English translation from JP 62632444.

JP2016-198402, Notice of Reasons for Rejection, dated Nov. 25, 2016, 7 pages—English, 7 pages—Japanese.

JP2016-198402, Notice of Reasons for Rejection, dated Mar. 21, 2017, 6 pages—English, 5 pages—Japanese.

JP-B-6263244, Proposed Claims, 2 pages—English.

PCT/JP2016/079962, International Search Report and Written Opinion, dated Dec. 20, 2016, 2 pages—English, 11 pages—Japanese.

PCT/JP2015/080764, International Search Report and Written Opinion, dated Feb. 2, 2016, 3 pages—English, 9 pages—Japanese.

Ishii, Hiroaki, et al., Efficacy and Physical Properties of Sunscreen Film, Oleoscience, 2009, vol. 9, No. 5, p. 183-188, ISSN: 1345-8949.

PCT/JP2017/014935 International Search Report and Written Opinion, dated Jul. 4, 2017, 3 pages—English, 10 pages—Japanese.

U.S. Appl. No. 16/095,457, Office Action dated Apr. 1, 2019, 8 pages.

U.S. Appl. No. 15/522,016, Office Action dated Mar. 25, 2019, 14 pages.

EP 15854207.6, Search Report dated May 4, 2018, 7 pages—English.

U.S. Appl. No. 15/522,016 Office Action dated Mar. 25, 2019, 13 pages.

Glenn Corp. ABIL®em 90, Emulsifier for the formulation of cosmetic W/O creams and lotions, Evonik Indusries, published Apr. 2008, p. 1-7.

EP 16853755.3, Extended European Search Report dated May 2, 2019, 9 pages—English.

* cited by examiner

SPRAYABLE SUNSCREEN COSMETIC

CROSS REFERENCE TO RELATED APPLICATIONS

This application relates to and claims priority as a § 371 national phase, from PCT/JP2016/079962 filed Oct. 7, 2017, the entire contents of which are incorporated herein by reference, which in turn claims priority from JP 2015-201595 filed Oct. 9, 2015 and JP 2016-198402 filed Oct. 6, 2016.

TECHNICAL FIELD

The present invention relates to a sprayable sunscreen cosmetic. More specifically, the present invention relates to a water-in-oil emulsified sunscreen cosmetic that does not turn white even immediately after being sprayed on skin, and that has the heretofore unknown property wherein, by coming into contact with water, perspiration or the like, the ultraviolet ray protection effect is improved relative to the effect immediately after being sprayed (applied).

BACKGROUND ART

Protecting the skin from damage due to ultraviolet rays is an important problem in skin care and body care, and various UV-care cosmetics for minimizing the harmful effects of ultraviolet rays on the skin have been developed. Sunscreen cosmetics, which are a type of UV-care cosmetic, are cosmetics that protect the skin from damage due to ultraviolet rays by containing an ultraviolet ray absorbing agent or an ultraviolet ray scattering agent, thereby blocking UVA and UVB rays from reaching the skin (Non-Patent Document 1).

As types of sunscreen cosmetics, formats in which a lotion stored in a container is taken in the hand and applied to the skin and formats in which the cosmetic is sprayed directly onto the skin are known, and various properties are required depending on the format. For example, for sprayable sunscreen cosmetics, it is necessary to prevent blockage of the nozzle due to aggregation of powder ingredients such as ultraviolet ray scattering agents.

Patent Document 1 describes an aerosol-type sunscreen cosmetic wherein the powder dispersibility is improved by dispersing an inorganic oxide powder such as an ultraviolet ray scattering agent in an oil-based liquid containing a specific lipophilic solvent (ester oil), alcohol and an ultraviolet ray absorbing agent. However, while lotion-type sunscreen cosmetics are spread by the hand, thus mitigating their whiteness, sprayable sunscreen cosmetics such as aerosols are often not spread after being sprayed on the skin, and are required to be transparent immediately after being sprayed. For this reason, they preferably do not contain ultraviolet ray scattering agents that cause whiteness.

However, in order to obtain excellent ultraviolet ray protection effects (high SPF (Sun Protection Factor) and high PA (Protection Grade of UVA)) in a sunscreen cosmetic that does not contain an ultraviolet ray scattering agent, it is necessary to add large quantities of ultraviolet ray absorbing agents for the UVA and UVB ranges, and the amounts of oil-based solvents (polar oils or the like) that are blended must also be increased in order to dissolve these ultraviolet ray absorbing agents, resulting in problems such as sensations of oiliness or stickiness when used.

Patent Document 2 discloses a spray-type sunscreen cosmetic that contains substantially no powder ingredients such as ultraviolet ray scattering agents, and that protects against ultraviolet rays in the UVA to UVB ranges by means of an ultraviolet ray absorbing agent. The document describes that a cosmetic providing a long-lasting sensation of freshness without causing coarseness is obtained by setting the blended amount of lower alcohols to 80 to 85 mass % and setting the blended amounts of silicone and water to about 5 mass % or less. However, it is difficult to dissolve all of the ultraviolet ray absorbing agents by blending in large quantities of alcohol, and there are concerns about problems such as the precipitation of the ultraviolet ray absorbing agent over time.

On the other hand, when sunscreen cosmetics that have been applied to skin come into contact with water or perspiration, the ultraviolet ray absorbing agents and ultraviolet ray scattering agents can flow out from the applied cosmetic, and decreases in ultraviolet ray protection effects are unavoidable. For example, even if a cosmetic contains large quantities of resins or film-forming agents in order to provide water resistance, it is still difficult to completely prevent the outflow of ultraviolet absorbing agents, ultraviolet scattering agents or the like. Additionally, it was thought that, even if the outflow of ultraviolet ray absorbing agents or the like could be entirely prevented, the resulting ultraviolet ray protection effects would never be superior to the effects immediately after application.

RELATED ART DOCUMENTS

Patent Documents

Patent Document 1: JP 2014-201541 A
Patent Document 2: JP 2014-224075 A

Non-Patent Documents

Non-patent Document 1: Shin-keshohingaku, 2nd edition, edited by Takeo Mitsui, 2001, published by Nanzando, pp. 497-504.

SUMMARY OF THE INVENTION

Problems to be Solved by the Invention

The present invention has the purpose of providing a sprayable sunscreen cosmetic that contains substantially no ultraviolet ray scattering agents which cause whiteness, that is transparent immediately after being applied/sprayed, and that has excellent ultraviolet ray protection effects and a good sensation when used, wherein the sprayable sunscreen cosmetic has the heretofore unknown, innovative property wherein the ultraviolet ray protection effects are not reduced, and the effects conversely improve, even when coming into contact with water, perspiration or the like.

Means for Solving the Problems

As a result of performing diligent research towards solving the aforementioned problem, the present inventors discovered that a sunscreen cosmetic having the novel properties of the aforementioned purpose can be obtained by blending an organically modified clay mineral and an oil phase thickener at a prescribed mass ratio with respect to a non-volatile liquid oil excluding silicone oils, and blending in a specific powder ingredient and a volatile oil, thereby arriving at the present invention.

In other words, the present invention provides a water-in-oil emulsified sunscreen cosmetic comprising:

(A) 6 to 40 mass % of an ultraviolet ray absorbing agent;
(B) an organically modified clay mineral;
(C) an oil phase thickener other than the aforementioned (B);
(D) a silicone-based surfactant having an HLB of less than 8;
(E) a spherical resin powder; and
(F) a volatile silicone oil;

wherein a ratio defined as [total amount of ingredient (B) and ingredient (C)]/[total amount of (G) non-volatile liquid oils other than silicone oils] is at least 0.04 and less than 0.68.

The sunscreen cosmetic of the present invention is particularly suitable for use by being sprayed with a spray device or the like.

Effects of the Invention

The sunscreen cosmetic of the present invention contains substantially no ultraviolet ray scattering agents and therefore does not become white even immediately after being sprayed on skin, and achieves excellent ultraviolet ray protection effects due to an ultraviolet ray absorbing agent. On the other hand, the dispersibility of the blended powders is improved, powder precipitation and solidification do not occur, and a light, smooth sensation can be provided without causing a feeling of oiliness or stickiness.

Furthermore, in the sunscreen cosmetic of the present invention, the ultraviolet ray protection effect after coming into contact with water, perspiration or the like is significantly improved in comparison to the effect immediately after the cosmetic is applied to the skin. In other words, the water-in-oil emulsified sunscreen cosmetic according to the present invention is an innovative sunscreen cosmetic having a property that is the opposite of what would be expected according to conventional technical knowledge in that the ultraviolet ray protection effect improves upon coming into contact with water, which has heretofore been considered to reduce the effectiveness of sunscreen cosmetics.

MODES FOR CARRYING OUT THE INVENTION

As mentioned above, the water-in-oil sunscreen cosmetic of the present invention is particularly suitable for use by being sprayed, and comprises (A) 6 to 40 mass % of an ultraviolet ray absorbing agent; (B) an organically modified clay mineral; (C) an oil phase thickener other than the aforementioned (B); (D) a silicone-based surfactant having an HLB of less than 8; (E) a spherical resin powder; and (F) a volatile silicone oil; wherein a ratio defined as [total amount of ingredient (B) and ingredient (C)]/[total amount of (G) non-volatile liquid oils other than silicone oils] is at least 0.04 and less than 0.68. The essential features of the present invention shall be described in detail below.

<(A) Ultraviolet Ray Absorbing Agent>

The (A) ultraviolet ray absorbing agent (hereinafter sometimes referred to simply as "ingredient (A)") that is blended in the water-in-oil emulsified sunscreen cosmetic according to the present invention may be chosen from among those that are normally blended in sunscreen cosmetics, and is not particularly limited. Specific examples include organic ultraviolet absorbing agents such as octyl methoxycinnamate (ethylhexyl methoxycinnamate), octocrylene, dimethicodiethyl benzalmalonate, polysilicone-15, t-butyl methoxydibenzoyl methane, ethylhexyl triazone, bis-ethylhexyloxyphenol methoxyphenyl triazine, diethylamino hydroxybenzoyl hexyl benzoate, bis-ethylhexyloxyphenol methoxyphenyl triazine, oxybenzone-3, methylene bis-benzotriazolyl tetramethylbutylphenol, polysilicone-15, phenylbenzimidazole sulfonic acid, homosalate and ethylhexyl salicylate.

In the cosmetic of the present invention, in order to achieve an excellent ultraviolet ray protection effect across a wide wavelength range from UVA to UVB even without containing an ultraviolet ray scattering agent, it is preferable to blend a combination of at least one each of an ultraviolet ray absorbing agent (UVA absorbing agent) having an absorption peak in the UVA range and an ultraviolet ray absorbing agent (UVB absorbing agent) having an absorption peak in the UVB range, or at least one ultraviolet ray absorbing agent having a wide absorption band across the UVA to the UVB ranges. However, in order to reliably achieve the specific effect of improving the ultraviolet ray protection effect when coming into contact with moisture or the like, it is preferable to include only an oil-soluble ultraviolet ray absorbing agent without blending in a water-soluble ultraviolet ray absorbing agent such as, for example, phenylbenzimidazole sulfonic acid.

The blended amount of the ingredient (A) is 6 mass % or more, preferably 6 to 40 mass %, more preferably 7 to 30 mass % with respect to the overall amount of the water-in-oil emulsified sunscreen cosmetic. If the blended amount of ingredient (A) is less than 6 mass %, then it is difficult to obtain sufficient ultraviolet ray protection effects, and even if more than 40 mass % is added, an increase in the ultraviolet ray protection effects commensurate with the blended amount cannot be expected, and the stability becomes worse.

<(B) Organically Modified Clay Mineral>

As the (B) organically modified clay mineral (hereinafter sometimes referred to simply as "ingredient (B)"), it is possible to favorably use a clay mineral modified by a quaternary ammonium salt type cationic surfactant, represented by the following formula (1), which is a type of colloidal hydrated ammonium silicate having a three-layered structure.

$$(X,Y)_{2-3}(Si,Al)_4O_{10}(OH)_2Z_{1/3}\cdot nH_2O \quad (1)$$

where X=Al, Fe(III), Mn(III) or Cr(III); Y=Mg, Fe(II), Ni, Zn or Li; and Z=K, Na or Ca.

Specifically, the ingredient can be obtained by treating, with a quaternary ammonium salt type cationic surfactant, a clay mineral which may be a natural or synthetic (in this case, an (OH) group in the formula is substituted with a fluorine) substance in the montmorillonite group, such as montmorillonite, saponite or hectorite (commercial products include Veegum, Kunipia, Laponite, etc.), or a synthetic mica known under the name of sodium silicic mica or sodium or lithium taeniolite (commercial products include Dimonite, manufactured by Topy Industries).

The quaternary ammonium salt type cationic surfactant used in this case is represented by the following general formula (2):

[Chemical Formula 1]

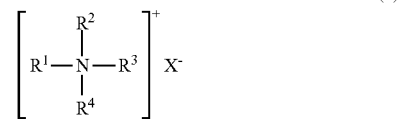

(2)

where $R^1$ represents a benzyl group or an alkyl group having 10 to 22 carbon atoms, $R^2$ represents an alkyl group having 10 to 22 carbon atoms or a methyl group, $R^3$ and $R^4$ represent alkyl groups or hydroxyalkyl groups having 1 to 3 carbon atoms, and X represents a halogen atom or a methylsulfate residue.

Examples of the quaternary ammonium salt type cationic surfactant include dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, dibehenyldihydroxyethylammonium chloride, and corresponding bromides and the like, and further thereto, dipalmitylpropylethylammonium methylsulfate and the like. When carrying out the present invention, one or more of these compounds may be freely chosen.

Representative examples of ingredient (B) include dimethyldistearylammonium hectorite, dimethylalkylammonium hectorite, benzyldimethylstearylammonium hectorite, distearyldimethylammonium-chloride-treated aluminum-magnesium silicate and the like. Of these, dimethyldistearylammonium hectorite is particularly preferred. As commercial products, Bentone 27 (benzyldimethylstearylammonium-chloride-treated hectorite, manufactured by Elementis Japan) and Bentone 38 (distearyldimethylammonium-chloride-treated hectorite, manufactured by Elementis Japan) are preferred.

The blended amount of ingredient (B) is 0.1 to 3 mass %, preferably 0.2 to 2 mass %, more preferably 0.4 to 1 mass % with respect to the overall amount of the water-in-oil emulsified sunscreen cosmetic. If the blended amount of ingredient (B) is less than 0.1 mass %, it is difficult to obtain sufficient stability, and if added in excess of 3 mass %, the viscosity becomes high and it is undesirable in terms of the texture, such as becoming heavy to spread over the skin.
<(C) Oil Phase Thickener>

The (C) oil phase thickener (hereinafter sometimes referred to simply as "ingredient (C)") is a substance (other than a substance that corresponds to ingredient (B)) that can adjust the viscosity of the oil phase. For example, dextrin fatty acid esters, sucrose fatty acid esters, and fatty acids or salts thereof and the like are preferable, and it is particularly preferable to blend two or more types chosen from the above.

Dextrin fatty acid esters are esters of dextrin or reduced dextrin with a higher fatty acid, which may be used without any particular restrictions as long as they are generally used in cosmetics. As the dextrin or reduced dextrin, one having an average degree of polymerization of sugars of 3 to 100 is preferably used. Additionally, as the constituent fatty acids in the dextrin fatty acid ester, a saturated fatty acid having 8 to 22 carbon atoms is preferably used. Specific examples include dextrin palmitate, dextrin oleate, dextrin stearate, dextrin myristate, dextrin (palmitate/2-ethylhexanoate) and the like.

As the sucrose fatty acid ester, one in which the fatty acid is straight or branched, saturated or unsaturated, and has 12 to 22 carbon atoms is preferably used. Specific examples include sucrose caprylic acid esters, sucrose capric acid esters, sucrose lauric acid esters, sucrose myristic acid esters, sucrose palmitic acid esters, sucrose stearic acid esters, sucrose oleic acid esters, sucrose erucic acid esters and the like.

The fatty acid may be solid at ambient temperature, and examples include myristic acid, palmitic acid, stearic acid, behenic acid and the like. Additionally, the fatty acid salt may be a calcium salt, a magnesium salt, an aluminum salt or the like of the above.

The blended amount of ingredient (C) is 0.1 to 15 mass %, preferably 0.2 to 10 mass %, more preferably 0.4 to 8 mass % with respect to the overall amount of the water-in-oil emulsified sunscreen cosmetic. If the blended amount of ingredient (C) is less than 0.1 mass %, then it is difficult to obtain sufficient stability, and if added in excess of 15 mass %, the viscosity becomes high and it is undesirable in terms of the texture, such as becoming heavy to spread over the skin.
<(D) Silicone-Based Surfactant Having an HLB of Less Than 8>

The (D) silicone-based surfactant (hereinafter sometimes referred to simply as "ingredient (D)") has a silicone backbone (polysiloxane structure) and is not particularly limited as long as it is a surfactant having an HLB of less than 8. For example, the use of a polyoxyalkylene-modified silicone, a polyoxyalkylene/alkyl-comodified silicone, a polyglycerin-modified silicone and/or a polyglycerin/alkyl-comodified silicone is preferred, and a polyoxyalkylene-modified silicone and a polyoxyalkylene/alkyl-modified silicone are particularly preferred.

The polyoxyalkylene-modified silicone used in the present invention has a straight or branched organopolysiloxane as the main backbone and has a polyoxyalkylene group in a side chain. For example, it may be a compound expressed by the following general formula (3).

[Chemical Formula 2]

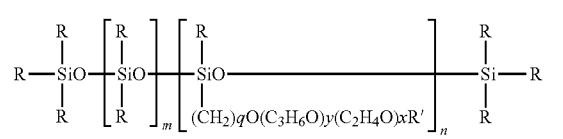

(3)

In general formula (3), R represents a phenyl group or an alkyl group having 1 to 3 carbon atoms (preferably a methyl group), R' represents hydrogen or an alkyl group having 1 to 12 carbon atoms (preferably hydrogen or a methyl group), q is 1 to 50 (preferably 3), m is 1 to 100, n and x are each 1 to 50, and y is 0 to 50. A suitable example of a polyoxyalkylene-modified silicone is KF-6017 (PEG-10 dimethicone, manufactured by Shin-Etsu Chemical).

Additionally, in the above-indicated formula (3), the organopolysiloxane main backbone may have another organopolysiloxane chain as a side chain. A suitable example of such a polyoxyalkylene-modified silicone is KF-6028

(PEG-9 polydimethylsiloxyethyl dimethicone, manufactured by Shin-Etsu Chemical).

The polyoxyalkylene/alkyl-modified silicone used in the present invention has a straight or branched organopolysiloxane as the main backbone and has a polyoxyalkylene group and an alkyl group having 4 or more carbon atoms in a side chain. For example, it may be a compound expressed by the following general formula (4).

[Chemical Formula 3]

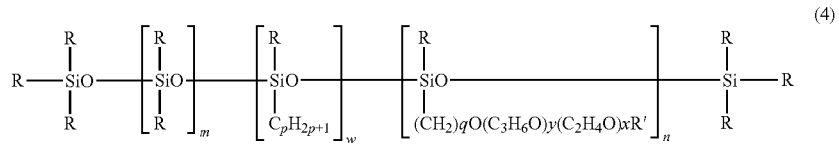

(4)

In general formula (4), R represents a phenyl group or an alkyl group having 1 to 3 carbon atoms (preferably a methyl group), R' represents hydrogen or an alkyl group having 1 to 12 carbon atoms (preferably hydrogen), p is 6 to 30 (preferably 10 to 18, more preferably 12 to 16), q is 1 to 50 (preferably 3), m is 1 to 100, n, w and x are each 1 to 50, and y is 0 to 50. A suitable example of a polyoxyalkylene/alkyl-comodified silicone is ABIL EM90 (cetyl PEG/PPG-10/1 dimethicone, manufactured by Evonik Goldschmidt).

Additionally, in the above-indicated formula (4), the organopolysiloxane main backbone may have another organopolysiloxane chain as a side chain. A suitable example of such a polyoxyalkylene/alkyl-modified silicone is KF-6038 (lauryl PEG-9 polydimethylsiloxyethyl dimethicone, manufactured by Shin-Etsu Chemical).

The polyglycerin-modified silicone may, for example, be the straight polyglycerin-modified silicone (=polyglycerin with silicones at both ends) expressed by the following formula (5):

[Chemical Formula 4]

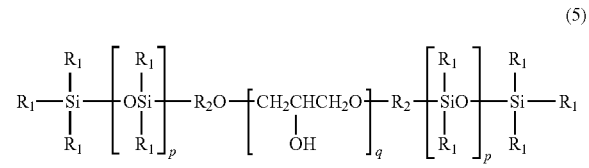

(5)

where $R_1$ represents a straight or branched alkyl group having 1 to 12 carbon atoms, or a phenyl group, $R_2$ represents an alkylene group having 2 to 11 carbon atoms, p is 10 to 120, and q is 1 to 11. Specific examples include bis-butyldimethicone polyglycerol-3 and the like.

The polyglycerin/alkyl-comodified silicone has a straight or branched organopolysiloxane as the main backbone and has a polyglycerin group and an alkyl group having 4 or more carbon atoms in a side chain. An example thereof is KF-6105 (lauryl polyglyceryl-3 polydimethylsiloxyethyl dimethicone, manufactured by Shin-Etsu Chemical).

The blended amount of ingredient (D) is 0.1 to 8 mass %, preferably 0.2 to 7 mass %, more preferably 0.4 to 5 mass % with respect to the overall amount of the water-in-oil emulsified sunscreen cosmetic. If the blended amount of ingredient (D) is less than 0.1 mass %, it is difficult to obtain sufficient stability, and if added in excess of 8 mass %, the viscosity becomes high and it is undesirable in terms of the texture, such as becoming heavy to spread over the skin.

<(E) Spherical Resin Powder>

By blending in the spherical resin powder (hereinafter sometimes referred to simply as "ingredient (E)") to the cosmetic of the present invention, it is possible to further improve the sensation when used and to obtain a good, smooth texture.

The spherical resin powder used in the present invention may be freely used without any particular limitations, as long as it can be used as a spherical resin powder in cosmetic products or the like in general. Examples include (meth)acrylic acid ester resin powders, polyamide resin powders (nylon powders), polyethylene powders, polystyrene powders, styrene/(meth)acrylic acid copolymer resin powders, benzoguanamine resin powders, polytetrafluoroethylene powders, cellulose powders, trimethyl silsesquioxane powders and the like (hereinafter referred to as "spherical organic resin powders"), as well as organopolysiloxane elastomer spherical powders or composite spherical powders having the same as base powders (hereinafter referred to as "spherical silicone resin powders"). Although the particle sizes or the like of the blended spherical resin powders are not particularly limited, one in which the particle size is, for example, approximately 1 to 50 may be favorably used. Additionally, these resin powders may be subjected to hydrophobization treatments.

An example of a commercially available spherical organic resin powder is Ganzpearl (manufactured by Aica Kogyo), and examples of commercially available spherical silicone resin powders include Trefil E-505C, Trefil E-506C, Trefil E-506S, Trefil HP40T (all manufactured by Toray Dow Corning Silicone), Tospearl 145A (manufactured by Toshiba Silicone), and silicone powders KSP-100 and KSP-300 (manufactured by Shin-Etsu Chemical) and the like.

In the present invention, it is possible to freely choose one or more of these spherical resin powders. In particular, it is preferable to blend a combination of a spherical organic resin powder and a spherical silicone resin powder. The ratio between the blended amounts of the spherical organic resin powder and the spherical silicone resin powder is preferably 3:1 to 1:3, more preferably 2:1 to 1:2, and even more preferably approximately 1:1 (for example, 1.5:1 to 1:1.5, or 1.2:1 to 1:1.2 or the like).

Although the blended amount of the (E) spherical resin powder is not particularly limited, it should preferably be 3 to 30 mass %, more preferably 5 to 25 mass %, and even more preferably 7 to 20 mass %.

<Oil>

The cosmetic of the present invention is a water-in-oil emulsified cosmetic, and thus must always contain an oil constituting the external phase (continuous phase). The oil in the present invention includes volatile oils and non-volatile oils.

<Volatile Oil>

The volatile oils that may be blended into the cosmetic of the present invention include volatile hydrocarbon oils and volatile silicone oils.

The volatile hydrocarbon oils are not particularly limited as long as they are hydrocarbon oils that are volatile at ambient temperature (25° C.) and are conventionally used in cosmetics and the like. Specific examples include isododecane, isohexadecane, hydrogenated polyisobutene and the like.

The volatile silicone oils include silicone oils that are volatile at ambient temperature and are conventionally used in cosmetics and the like. Examples include volatile straight silicone oils (volatile dimethicones) and volatile cyclic silicone oils (volatile cyclodimethicones). Examples of volatile dimethicones include low-viscosity (e.g., a viscosity of approximately 100 to 500 mPa·s at 30° C.) dimethylpolysiloxanes such as decamethyl tetrasiloxane or the like, and commercial products include KF-96L-1.5 cs and KF-96-2 cs (both manufactured by Shin-Etsu Chemical) or the like. An example of a volatile cyclomethicone is decamethyl cyclopentasiloxane (D5) or the like.

The cosmetic of the present invention contains, as an essential ingredient, (F) a volatile silicone oil (hereinafter sometimes referred to simply as "ingredient (F)") as a volatile oil. By adjusting the volatility by blending in a volatile silicone oil, it is possible to obtain a cosmetic that has excellent properties in terms of the lightness when spreading the cosmetic and the lack of a sense of filminess. Additionally, when a volatile dimethicone is blended in as the ingredient (F), it is possible to obtain a cosmetic with an even better texture in comparison to the case in which only a volatile cyclomethicone is added. While the proportion of the total blended amount of the volatile oils that is occupied by the volatile silicone oil is not particularly limited, it may, for example, be 50 mass % or more, such as 60 mass % to 80 mass %.

Although the blended amount of the (F) volatile silicone oil in the cosmetic of the present invention is not particularly limited, it should be 1 to 40 mass %, preferably 5 to 30 mass %, more preferably 8 to 30 mass %.

<Non-Volatile Liquid Oil>

In the present specification, the "non-volatile liquid oil" refers to a liquid oil that does not exhibit volatility at ambient temperature (25° C.) and ambient pressure (1 atm (9.8×10$^4$ Pa)) (for example, oils having a boiling point of approximately 200° C. or higher at ambient pressure are included), that is fluid at ambient temperature and ambient pressure, and that is not solid, including silicone oils and non-volatile oils other than silicone oils (such as hydrocarbon oils, ester oils and the like).

In the present invention, the (G) non-volatile liquid oils other than silicone oils will be referred to as ingredient (G). The (G) non-volatile liquid oil ingredient (excluding silicone oils) may include oil-soluble ultraviolet ray absorbing agents corresponding to ingredient (A). Therefore, in the present invention, there may be cases in which all of ingredient (G) comprises the (A) oil-soluble ultraviolet ray absorbing agent.

Non-volatile liquid oils that may be included in ingredient (G) but do not correspond to (A) ultraviolet ray absorbing agents include, for example, liquid oils and fats such as hydrocarbon oils, vegetable oils and the like, ester oils, and macromolecular polyoxyalkylene glycols.

Specific examples include liquid oils and fats such as linseed oil, camellia oil, macadamia nut oil, corn oil, olive oil, avocado oil, sasanqua oil, castor oil, safflower oil, apricot kernel oil, cinnamon oil, jojoba oil, grape oil, almond oil, rapeseed oil, sesame oil, sunflower oil, wheat germ oil, rice germ oil, rice bran oil, cottonseed oil, soybean oil, peanut oil, tea seed oil, evening primrose oil, egg yolk oil, liver oil, triglycerin, glyceryl trioctanoate and glyceryl tri-isopalmitate; ester oils including octanoic acid esters such as cetyl octanoate, iso-octanoic acid esters such as glyceryl tri-2-ethylhexanoate and pentaerythritol tetra-2-ethylhexanoate, lauric acid esters such as hexyl laurate, myristic acid esters such as isopropyl myristate and octyldodecyl myristate, palmitic acid esters such as octyl palmitate, stearic acid esters such as isocetyl stearate, isostearic acid esters such as isopropyl isostearate, isopalmitic acid esters such as octyl isopalmitate, oleic acid esters such as isodecyl oleate, adipic acid diesters such as diisopropyl adipate, sebacic acid diesters such as diethyl sebacate, and diisotearyl malates such as diisotearyl malate; hydrocarbon oils such as liquid paraffin and squalane; and polyoxybutylene polyoxypropylene glycol.

<Ratio Defined as [Total Amount of Ingredient (B) and Ingredient (C)]/[Total Amount of Ingredient (G)]>

In the water-in-oil emulsified sunscreen cosmetic according to the present invention, the total amount of ingredient (B) and ingredient (C), which are involved in viscosity adjustment of the oil phase, must be in a prescribed ratio with respect to the total amount of the (G) non-volatile liquid oils other than silicone oils.

In other words, the ratio of [total amount of ingredient (B) and ingredient (C)]/[total amount of (G) non-volatile liquid oils other than silicone oils] (hereinafter sometimes referred to as "oil phase thickener ratio") must be at least 0.04 and less than 0.68, and furthermore, this ratio is more preferably at least 0.045 and less than 0.5. If the ratio is less than 0.04 or at least 0.68, then improvements in the ultraviolet ray protection effects due to coming into contact with water are not observed.

<Optional Ingredients>

In addition to the above-mentioned essential ingredients (A) to (G), the present invention may further contain (H) an oil-soluble film-forming agent (hereinafter sometimes referred to simply as "ingredient (H)"). By blending in ingredient (H), the resistance of the ultraviolet absorbing agent to outflow or to being rubbed off by clothing or the like can be raised.

The ingredient (H) is not particularly limited as long as it is normally used in cosmetics, and specific examples include PVP-based film-forming agents such as polyvinylpyrrolidone (PVP), PVP/dimethylaminoethyl methacrylic acid copolymers, PVP/eicosene copolymers, PVP/ethyl methacrylate/methacrylic acid copolymers, PVP/hexadecene copolymers, PVP/VA copolymers, PVP/vinyl acetate/itaconic acid copolymers and styrene/PVP copolymers; acrylic acid-based film-forming agents such as ethyl acrylate/amide acrylate/acrylic acid copolymers, ethyl acrylate/butyl acrylate copolymers, ethyl acrylate/ethyl methacrylate copolymers, ethyl acrylate/methacrylic acid copolymers, ethyl acrylate/methyl methacrylate copolymers, octyl acrylate/vinyl acetate copolymers, octyl acrylate/styrene copolymers, butyl acrylate/vinyl acetate copolymers, butyl acrylate/ethyl hydroxymethacrylate copolymers, butyl acrylate/methyl methacrylate copolymers, methoxyethyl acrylate/hydroxyethyl acrylate/butyl acrylate copolymers, lauryl acrylate/vinyl acetate copolymers, polyethyl acrylate, polybutyl acrylate and polystyrene acrylic acid resins; vinyl acetate-based film-forming agents such as polyvinyl acetate; methacrylic acid-based film-forming agents such as polymethyl methacrylate, methyl methacrylate/butyl acrylate/octyl acrylate and vinylpyrrolidone/N,N'-dimethylamino methacrylate copolymer diethyl sulfate copolymers; vinyl methyl ether-based film-forming agents such as vinyl methyl ether/ethyl maleate copolymers and vinyl methyl ether/butyl maleate copolymers; styrene-based film-forming agents such as styrene/methylstyrene/indene copolymers; alkyd resin-based film-forming agents such as cyclohexane-based alkyd resins; and silicone resin-based film-forming agents such as trimethylsiloxysilicate. Of these, trimethylsiloxysilicate is preferable in terms of water resistance and oil resistance.

When blending in ingredient (H), the blended amount thereof should preferably be an amount such that the ratio defined as [amount of ingredient (H)]/[total amount of (G) non-volatile liquid oils other than silicone oils] (hereinafter sometimes referred to as the "film-forming agent ratio") is less than 0.5. If the ratio is 0.5 or higher, there is a tendency for the filminess to become strong and the sensation when used and the washability to be reduced. Additionally, although there are not particular restrictions on the lower limit of the film-forming agent ratio, it should preferably be at least 0.01 in order to obtain sufficient effects due to the blending of the film-forming agent.

The present invention may further contain (I) a polyoxyethylene/polyoxypropylene dialkyl ether (hereinafter sometimes referred to simply as "ingredient (I)").

Ingredient (I) is a dialkyl ether of a random or block copolymer of polyoxyethylene and polyoxypropylene, a specific example being a dimethyl ether of a random polyoxyethylene (14) polyoxypropylene (7) copolymer. The blended amount of ingredient (I) should preferably be 0.001 to 5 mass % with respect to the overall amount of the water-in-oil emulsified sunscreen cosmetic.

The water-in-oil emulsified sunscreen cosmetic of the present invention may be produced by a conventional method and may contain, in addition to the above-mentioned essential ingredients, ingredients that are normally used in cosmetics. For example, it is possible to appropriately add, as needed, whiteners, humectants, antioxidants (e.g., 2,6-t-buyl-4-methylphenol or the like), lipophilic active agents, surface active agents, water phase thickeners, alcohols, non-spherical powder ingredients, colorants, hydrophilic active agents and the like.

Although the cosmetic of the present invention has suppressed whiteness at the time of spraying due to the feature of containing substantially no ultraviolet ray scattering agents, this does not preclude the possibility of adding a small amount of an ultraviolet ray scattering agent within a range allowing the purpose of the present invention to be achieved. For example, a cosmetic having even higher ultraviolet ray protection effects due to the blending of 2 mass % or less, or about 1 mass % or less, of an ultraviolet ray scattering agent would still be within the scope of the present invention.

The water-in-oil emulsified sunscreen cosmetic of the present invention is particularly suited to being provided as a sprayable sunscreen cosmetic that is loaded into a dispenser or an aerosol container and used by being sprayed from a nozzle.

The cosmetic loaded into the dispenser container is sprayed from the nozzle of the dispenser in the form of a mist. An aerosol container may have the cosmetic of the present invention as a stock solution, and may be filled with said stock solution and a propellant.

The propellant that is used in the present invention is not particularly limited as long as it is a propellant that can be used in aerosol products in general. For example, various types of liquefied gases such as liquefied petroleum gas (LPG), dimethyl ether, or mixtures of liquefied petroleum gas and dimethyl ether, or compressed gases such as nitrogen gas or carbon dioxide gas may be used. LPG is liquefied petroleum gas that is mainly composed of propane, butane and isobutane.

The cosmetic of the present invention is applicable not only to skin-care cosmetics, but also to makeup cosmetics and makeup bases, such as foundations, that are provided with a sunscreen effect.

EXAMPLES

While the present invention will be explained in further detail by providing specific examples below, the present invention is not to be construed as being limited to the following examples. Additionally, the amounts in the following examples and the like are expressed in mass % where not stated otherwise.

The water-in-oil emulsified sunscreen cosmetics having the compositions indicated in the following Tables 1 and 2 were prepared by heating and melting the oil-based ingredients and dispersing the powders therein, then adding the separately dissolved water phase thereto, and emulsifying by means of a stirring treatment. The cosmetics of each of the obtained examples were evaluated in the following categories.

Visual observations were made for the following categories 1 and 2.
1. Powder Precipitation and Solidification in Stock Solution
Evaluation Criteria:
 Good: Precipitation and solidification of powders did not occur in cosmetic stock solution.
Poor: Precipitation and solidification of powders occurred in cosmetic stock solution.
2. Powder Redispersibility (After Letting Stand for 12 Hours in a State of Being Loaded in an Aerosol Container)
Good: Powders redispersed well when the container was shaken.
Poor: Aggregated powders did not redisperse even when the container was shaken.
3. Measurement of Ultraviolet Ray Protection Effect
 Cosmetics (samples) of each example were dripped, at a rate of 2 mg/cm$^2$, onto S plates (5×5 cm V-groove PMMA plate, SPFMASTER-PA01), applied with the finger for 60 seconds, dried for 15 minutes, then the absorbances thereof were measured using a Hitachi U-3500 self-recording spectrophotometer. Glycerin, which does not absorb ultraviolet rays, was used as the control, and the absorbance (Abs) was computed by the following formula.

$$Abs=-\log(T/To)$$

T: sample transmittance, To: glycerin transmittance

The measured plates were fully immersed in water having a hardness of 50 to 500, and allowed to soak in the water for 30 minutes. Thereafter, the plates were dried for about 15 to 30 minutes until the water droplets on the surfaces disappeared, the absorbances were measured again, and the Abs change percentage (see formula below) was computed, as the ultraviolet ray protection performance improvement effect, from the Abs integral values before and after the water bath.

Ultraviolet ray protection performance improvement effect:

$$\text{Abs change percentage (\%)} = (\text{Abs integral value after water bath})/(\text{Abs integral value before water bath}) \times 100$$

In the present invention, an improvement in the ultraviolet ray protection effect is defined as having occurred when the Abs change percentage exceeds 100(%).

Regarding the following categories 4 and 5, evaluations were made by ten expert panelists under the following criteria:

4. Non-Stickiness and Smoothness
5. Lightness of Spreading and Lack of Filminess Evaluation Criteria:
A: Seven or more panelists evaluated the results as "good".
B: Five or six panelists evaluated the results as "good".
C: Four or fewer panelists evaluated the results as "good".

6. Overall Evaluation

Based on the results of the above-mentioned evaluations, the cosmetics of each of the examples indicated in Table 2 were evaluated overall according to the following criteria:

Evaluation Criteria:
+++: Abs change percentage higher than 100(%), and "good" or "A" in all four other evaluation categories.
++: Abs change percentage higher than 100(%), and "good" or "A" in three of the other evaluation categories.
+: Abs change percentage higher than 100(%), and "good" or "A" in one or two of the other evaluation categories.
−: Abs change percentage not higher than 100(%).

TABLE 1

|  | Comp. Ex. 1 | Comp. Ex. 2 | Ex. 1 | Ex. 2 | Ex. 3 | Ex. 4 |
|---|---|---|---|---|---|---|
| 2-Ethylhexyl para-methoxycinnamate | 8 | 8 | 8 | 8 | 8 | 8 |
| Octocrylene | 2 | 2 | 2 | 2 | 2 | 2 |
| bis-Ethylhexyloxyphenol methoxyphenyl triazine | 1.5 | 1.5 | 1.5 | 1.5 | 1.5 | 1.5 |
| Diethylamino hydroxybenzoyl hexyl benzoate | 2 | 2 | 2 | 2 | 2 | 2 |
| Polysilicone-15 | — | 5 | 5 | 5 | 5 | 5 |
| Polyoxybutylene polyoxypropylene glycol | 2 | 2 | 2 | 2 | 2 | 2 |
| Isostearic acid | 0.5 | 0.5 | 0.5 | 0.5 | 0.5 | 0.5 |
| Cetyl ethylhexanoate | 2 | 2 | 2 | 2 | 2 | 2 |
| Isopropyl myristate | 5 | 5 | 5 | 5 | 5 | 5 |
| Dimethicone (non-volatile) | 2 | 2 | 2 | 2 | 2 | 2 |
| Diisopropyl sebacate | 5 | 5 | 5 | 5 | 5 | 5 |
| Lauryl PEG-9 polydimethylsiloxyethyl dimethicone | 3 | 3 | 3 | 3 | 3 | 3 |
| Dextrin palmitate | — | 0.01 | 1 | 1 | 1 | 1 |
| Distearyldiammonium hectorite | — | 0.1 | 0.5 | 0.5 | 0.5 | 0.5 |
| Volatile cyclomethicone (1) | 8.5 | 8.5 | 8.5 | 8.5 | 8.5 | 8.5 |
| Isododecane | 20.15 | 15.79 | 14.26 | 8.4 | 3.4 | 4.4 |
| Spherical silicone resin powder (2) | 6 | 6 | 6 | 6 | 6 | 10 |
| Spherical organic resin powder (3) | 5 | 5 | 5 | 10 | 15 | 10 |
| Talc | 0.1 | 0.1 | 0.1 | 0.1 | 0.1 | 0.1 |
| Ion-exchanged water | bal | bal | bal | bal | bal | bal |
| EDTA-3Na, 2H2O | 0.2 | 0.2 | 0.2 | 0.2 | 0.2 | 0.2 |
| Phenylbenzimidazole sulfonic acid | 2.5 | — | — | — | — | — |
| Polyoxyethylene (14) polyoxypropylene (7) dimethyl ether | 0.5 | 0.5 | 0.5 | 0.5 | 0.5 | 0.5 |
| Triethanolamine | 1.5 | — | — | — | — | — |
| Ethanol | 10 | 10 | 10 | 10 | 10 | 10 |
| Glycerin | 2 | 2 | 2 | 2 | 2 | 2 |
| Total | 100 | 100 | 100 | 100 | 100 | 100 |
| Powder precipitation and solidification in stock solution | poor | good | good | good | good | good |
| Powder redispersibility | poor | good | good | good | good | good |
| Abs change percentage (%) | 84.8 | 84.8 | 103.7 | 105.6 | 106.7 | 110.5 |
| Stickiness, smoothness | A | A | C | C | B | A |

(1) Decamethylcyclopentasiloxane
(2) Methylsiloxane network polymer
(3) Polymethyl methacrylate

TABLE 2

|  | Ex. 5 | Ex. 6 | Ex. 7 | Ex. 8 | Ex. 9 | Comp. Ex. 2 |
|---|---|---|---|---|---|---|
| 2-Ethylhexyl para-methoxycinnamate | 8 | 8 | 8 | 8 | 8 | 8 |
| Octocrylene | 2 | 2 | 2 | 2 | 2 | 2 |
| bis-Ethylhexyloxyphenol methoxyphenyl triazine | 1.5 | 1.5 | 1.5 | 1.5 | 1.5 | 1.5 |
| Diethylamino hydroxybenzoyl hexyl benzoate | 2 | 2 | 2 | 2 | 2 | 2 |
| Polysilicone-15 | 5 | 5 | 3 | — | 3 | 5 |
| Polyoxybutylene polyoxypropylene glycol | 2 | 2 | 2 | 2 | 2 | 2 |
| Isostearic acid | 0.5 | 0.5 | 0.5 | 0.5 | 0.5 | 0.5 |
| Cetyl ethylhexanoate | 2 | 2 | 2 | 2 | 2 | 2 |
| Isopropyl myristate | 5 | 5 | 5 | 5 | 5 | 5 |
| Dimethicone (non-volatile) | 2 | 2 | 2 | 2 | 2 | 2 |
| Diisopropyl sebacate | 5 | 5 | 5 | 5 | 5 | 5 |
| Lauryl PEG-9 polydimethylsiloxyethyl dimethicone | 3 | 3 | 3 | 3 | 3 | 3 |
| Dextrin palmitate | 1 | 1 | 1 | 1 | 1.5 | 0.01 |
| Distearyldiammonium hectorite | 0.5 | 0.5 | 0.5 | 0.5 | 0.5 | 0.1 |
| Trimethylsiloxysilicate | — | — | — | — | 3 | — |
| Volatile cyclomethicone (1) | 8.5 | — | — | — | — | 8.5 |
| Volatile dimethicone | — | 14 | 13 | 13 | 12.5 | — |
| Isododecane | 9 | 3 | 6 | 6 | 3 | 15.79 |
| Spherical silicone resin powder (2) | 8 | 8 | 8 | 8 | 8 | 6 |
| Spherical organic resin powder (3) | 8 | 8 | 8 | 8 | 8 | 5 |
| Talc | 0.1 | 0.1 | 0.1 | 0.1 | 0,1 | 0.1 |
| Ion-exchanged water | bal | bal | bal | bal | bal | bal |
| EDTA-3Na, 2H2O | 0.2 | 0.2 | 0.2 | 0.2 | 0.2 | 0.2 |
| Polyoxyethylene (14) polyoxypropylene (7) dimethyl ether | 0.1 | 0.1 | 0.1 | 0.1 | 0.1 | 0.5 |
| Ethanol | 10 | 10 | 10 | 10 | 10 | 10 |
| Glycerin | 2 | 2 | 2 | 2 | 2 | 2 |
| Total | 100 | 100 | 100 | 100 | 100 | 100 |
| Powder precipitation and solidification in stock solution | good | good | good | good | good | good |
| Powder redispersibility | good | good | good | good | good | good |
| Abs change percentage (%) (standing water) | 104.9 | 103.1 | 105.1 | 105.1 | 107.2 | 84.8 |
| Stickiness, smoothness | A | A | A | A | A | A |
| Lightness to spread, filminess | C | B | A | A | B | A |
| Overall evaluation | ++ | ++ | +++ | +++ | ++ | − |

(1) Decamethylcyclopentasiloxane
(2) Methylsiloxane network polymer
(3) Polymethyl methacrylate As shown in Tables 1 and 2, Comparative Example 1, which contained a water-soluble ultraviolet ray absorbing agent as ingredient (A) and did not contain a (B) organically modified clay mineral or a (C) oil phase thickener, had poor powder dispersibility and ultraviolet ray protection capability improvement effects were also not observed. In Comparative Example 2, in which the water-soluble ultraviolet ray absorbing agent in Comparative Example 1 was replaced with an oil-soluble ultraviolet ray absorbing agent (polysilicone-15), and a clay mineral and an oil phase thickener were added, the powder dispersibility improved, but the blended amounts of the (B) organically modified clay mineral, the (C) oil phase thickener and the (G) non-volatile liquid oils other than silicone oils did not fulfill the prescribed relationship, and ultraviolet ray protection improvement effects were not observed. In Examples 1 to 4, in which the clay mineral and the oil phase thickener were increased, the properties of good powder dispersibility and improved ultraviolet ray protection effects were observed. Additionally, in Examples 2-4 in which the blended amounts of the spherical resin powders were changed, the sensation when used was improved by increasing the blended amount of the spherical resin powders and adjusting the ratio between the blended amounts of the spherical organic resin powder and the spherical silicone resin powder.

Example 5, in which volatile cyclomethicone was blended, and Examples 6-9, in which the same was replaced with volatile dimethicone, all had good texture (stickiness and smoothness) and powder dispersibility, and had the property wherein the ultraviolet ray protection effect improved upon coming into contact with water. In particular, Examples 6-9, which contained volatile dimethicone as the volatile silicone oil, improved by becoming light to spread and having a texture lacking filminess.

In Example 9, in which a film-forming agent was blended, a slight deterioration was observed in the sensation when used, but the advantageous property wherein the ultraviolet ray protection effect improved upon coming into contact with water was obtained. Additionally, the powder redispersibility was markedly superior.

The invention claimed is:

1. A water-in-oil emulsified sunscreen cosmetic, comprising:
    (A) 6 to 40 mass % of an ultraviolet ray absorbing agent;
    (B) an organically modified clay mineral;
    (C) an oil phase thickener selected from the group consisting of dextrin fatty acid esters, sucrose fatty acid esters, and fatty acids solid at ambient temperature and salts thereof;
    (D) a silicone-based surfactant having an HLB of less than 8;
    (E) a spherical resin powder;
    (F) a volatile silicone oil; and
    (G) one or more non-volatile liquid oils other than silicone oils;
    wherein a ratio of [total amount of ingredient (B)+ingredient (C)]/[a total amount of (G) non-volatile liquid oils other than silicone oils] is at least 0.04 and less than 0.68.

2. The water-in-oil emulsified sunscreen cosmetic, as in claim 1, wherein: the (F) volatile silicone is volatile dimethicone.

3. The water-in-oil emulsified sunscreen cosmetic, as in claim 1, which is used by being sprayed.

4. The water-in-oil emulsified sunscreen cosmetic, as in claim 1, wherein: the (E) spherical resin powder is a 3:1 to 1:3 mixture of a spherical organic resin powder and a spherical silicone resin powder.

5. The water-in-oil emulsified sunscreen cosmetic, as in claim 1, wherein: the (A) ultraviolet ray absorbing agent consists only of an oil-soluble ultraviolet ray absorbing agent.

6. The water-in-oil emulsified sunscreen cosmetic, as in claim 4, wherein: the (A) ultraviolet ray absorbing agent is at least one substance chosen from among octyl methoxycinnamate, octocrylene, bis-ethylhexyloxyphenol methoxyphenyl triazine, diethylamino hydroxybenzoyl hexyl benzoate and polysilicone-15.

7. The water-in-oil emulsified sunscreen cosmetic, as in claim 1, further comprising: (H) an oil-soluble film-forming agent.

8. The water-in-oil emulsified sunscreen cosmetic, as in claim 1, further comprising:
    (I) a dialkyl ether of a random or block copolymer of polyoxyethylene and polyoxypropylene.

* * * * *